(12) United States Patent
Kolattukudy et al.

(10) Patent No.: US 8,211,446 B2
(45) Date of Patent: Jul. 3, 2012

(54) IN VITRO MODEL OF LATENT MYCOBACTERIAL INFECTION

(75) Inventors: Pappachan E. Kolattukudy, Orlando, FL (US); Tatiana Sirakova, Orlando, FL (US); Jaiyanth Daniel, Orlando, FL (US); Chirajyoti Deb, Orlando, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 0 days.

(21) Appl. No.: 12/870,952

(22) Filed: Aug. 30, 2010

(65) Prior Publication Data

US 2011/0033915 A1 Feb. 10, 2011

Related U.S. Application Data

(62) Division of application No. 12/107,146, filed on Apr. 22, 2008, now Pat. No. 8,012,492.

(60) Provisional application No. 60/914,838, filed on Apr. 30, 2007.

(51) Int. Cl.
*A61K 39/04* (2006.01)
*A61K 39/02* (2006.01)
*C12Q 1/02* (2006.01)

(52) U.S. Cl. ............... 424/248.1; 424/234.1; 435/29; 435/32

(58) Field of Classification Search ............ 435/29, 435/32, 325, 366, 372; 424/234, 248.1
See application file for complete search history.

*Primary Examiner* — Rodney P. Swartz
(74) *Attorney, Agent, or Firm* — Timothy H. Van Dyke; Beusse, Wolter, Sanks, Mora & Maire, P.A.

(57) ABSTRACT

A method of inducing latency in *Mycobacterium* permits preparation of an in vitro model system of latent mycobacterial infection. Latency is induced in a pure culture of *Mycobacterium* by exposing it to multiple stress conditions, including a low nutrient culture medium without glycerol, a low pH, a relatively high level of carbon dioxide and a relatively low gas phase oxygen level. An in vitro model of mycobacterial infection employs macrophages induced from THP1 cells which are then infected with *Mycobacterium*. The infected macrophages are grown under hypoxic conditions to induce latency in the mycobacteria. The in vitro model of infection is useful in evaluating compounds for activity against latent mycobacteria.

2 Claims, 18 Drawing Sheets

(a)

(b)

0 days 3 days

IN VITRO MODEL OF LATENT MYCOBACTERIAL INFECTION

RELATED APPLICATION

This application is a division of U.S. application Ser. No. 12/107,146 which was filed on Apr. 22, 2008, and which claimed priority from U.S. provisional application Ser. No. 60/914,838, filed on Apr. 30, 2007.

FIELD OF THE INVENTION

The present invention relates to the field of infectious diseases and, more particularly, to a pure culture of *Mycobacterium* which exhibits latency, including resistance to rifampicin and storage of increased lipids, and to a method for generating such a culture.

BACKGROUND OF THE INVENTION

Tuberculosis (TB) remains the leading cause of preventable deaths in the world with 100 million new infections and two million deaths each year. TB is caused by *Mycobacterium tuberculosis* (hereinafter also referred to by the abbreviation "Mtb"), an acid-fast *bacillus* that is transmitted primarily via the respiratory route. The aerosol containing the pathogen is released from people with active TB when they cough or sneeze. When a person breathes in the pathogen it enters the alveolar macrophages via a variety of receptors. Mtb multiplies within the vacuoles in the macrophage, avoids fusion with the acidic lysosomes and eludes the host defenses. As the host defense system senses the multiplying pathogen and mounts its immune defense, the pathogen goes into a non-replicating, drug-resistant, latent state. The protective response by the immune system at the site of infection results in the formation of a granuloma that contains the infection and prevents its spread. Live bacilli have reportedly been isolated from granulomas or tubercles in the lungs of persons with clinically inactive tuberculosis, regarded as the latent form of TB, indicating that the organism can persist in granulomatous lesions for decades. It is estimated that one-third of the world population has latent TB. These individuals are asymptomatic latent carriers who exhibit no signs of disease. Their risk for reactivation is estimated to be 2-23% over their life time. One study concluded that a 25 year old with latent TB has a 7.3% life time risk of reactivation. The risk increases dramatically for persons coinfected with HIV, more like 10% per year. Thus, the advent of AIDS greatly amplified the TB threat to human health. The deadly partnership between TB and AIDS, especially with multi- and extremely drug-resistant TB, is contributing to a dramatic rise in TB cases worldwide leading to a grave situation. The emergence and spread of multi-drug resistant and extremely drug-resistant TB is widely recognized as a major threat to public health.

The ability of the pathogen to go into the drug-resistant latent state is a major road block to the eradication of TB. It is known that latent Mtb persists in a non-replicating state. Antibiotics used to treat bacterial infection are usually active against growing bacteria but not against the dormant pathogen. Correlation between antibiotic activity and bacterial growth state in streptomycin-dependent Mtb was shown almost 30 years ago. The antibiotic-resistance of non-growing bacteria is due to changes in bacterial metabolism or physiological state and is described as phenotypic resistance. The phenotypic resistance has been classified into three types based on the physiological state of bacteria as stationary phenotypic resistance, persister phenotypic resistance and phenotypic resistance in dormant bacteria. Mtb displays dormancy-related phenotypic resistance which is demonstrated by the Cornell mouse model. Traditionally, the phenotypic resistance is exemplified by resistance to the antibiotic Rifampicin (Rif) and is regarded as one of the hallmarks of latent TB. The mechanism of phenotypic resistance in dormant Mtb is not clearly understood.

Development of drugs that can effectively kill dormant Mtb is of vital importance for the eradication of TB. If such drugs would prevent the pathogen from surviving in a drug-resistant state, a combination of such drugs with currently used antibiotics could drastically shorten the period of treatment for complete cure and lead to global eradication of TB. For this purpose, we need to identify processes that are necessary for the pathogen to go into dormancy, survive under the nonreplicating drug-resistant state, and get reactivated when the immune system of the host is weakened. Such steps, essential for the latent pathogen, could offer ideal targets for novel antilatency drugs that can eliminate the dormant pathogen. To achieve these objectives we explored the biochemical processes that the pathogen uses to survive for such long periods under a latent state. It has been known for many decades that Mtb in the host uses fatty acids as the major source of energy. It is well known that glyoxylate cycle is used by organisms that live on fatty acids. In recent years the important role of isocitrate lyase, a key enzyme uniquely used in the glyoxylate cycle, was shown to be required for the persistence of Mtb in the host demonstrating the central role played by fatty acid catabolism in persistence. However, the source of fatty acids used by the pathogen remains unclear. We postulated that the pathogen probably stores energy as triacylglycerol (TG) as it goes into dormancy and uses this stored energy to survive the long dormant period at very low metabolic rates as many living organisms such as hibernating animals, seeds and spores do for similar purposes. We began to identify the likely gene products that the pathogen uses to store TG and to release the fatty acids for catabolism. We also initiated the development of an in vitro dormancy model to test the hypothesis that lipid storage and mobilization are of importance for latency, a model that can be adapted for screening antilatency drug candidates.

TG is an important storage form of lipid that accumulates in species belonging to the actinomycetes family, particularly Mtb. Intracellular TG inclusion bodies were detected in mycobacteria isolated from organ lesions and *Mycobacterium bovis* BCG was reported to preferentially use TG within macrophages indicating that TG is probably used as an energy source by Mtb during the course of the disease. We have shown that TG accumulates when Mtb is subjected to hypoxia or nitric oxide treatment that led to a dormancy-like state in culture. We identified fifteen members of a novel class of diacylglycerol acyltransferase genes which we designated as tgs (triacylglycerol synthase). Several of the tgs genes were significantly upregulated under hypoxic conditions and under nitric oxide treatment, particularly those that show the highest TG synthase activity when expressed in *E. coli*. We identified Rv3130c as the prime gene in the biosynthesis of TG in the bacterium under in vitro dormancy-like conditions. Our hypothesis was strongly supported by a important recent report on the W/Beijing lineage of Mtb strains which has been associated with the increasing incidence of multi-drug resistant (MDR) TB epidemic in Asia. The W/Beijing strains were shown to overproduce TG and the Rv3130c gene was constitutively upregulated along with the dormancy regulator protein DosR. The authors suggested that constitutive accumulation of TG by this strain may confer an adaptive advantage for growth in microaerophilic or anaerobic environments and thus be related to the epidemiological spread of this strain.

Our hypothesis concerning the importance of Rv3130c is strongly supported by the remarkable finding by our collaborators. A recently developed two step multiplex and real time PCR method was adapted for reliable quantitative gene profiling of the small amount of latent Mtb expected to be found in infected animal and human host lung tissues. Remarkably, tgs1 (Rv3130c) was by far the most upregulated gene in the pathogen within the host, while dosR and aceAa that are well-known to be involved in dormancy, were much less induced. Many organisms use waxy esters (WE) as the major form of energy storage. Mtb also stores WE but the genes involved in the synthesis of WE and the growth conditions that cause its accumulation have not been identified. The basic mechanisms used for biosynthesis of WE were first elucidated in our laboratory several decades ago and the enzymatic strategy described more recently. We have recently shown that Rv3391 and Rv1543 encode acyl-CoA reductases involved in WE synthesis in Mtb. Rv3391 has been reported to be upregulated under nutrient stress conditions. We found that WE accumulates under stress conditions that lead to a dormancy-like state and the accumulated WE is utilized upon starvation. This utilization was reduced in lipY mutant, indicating the involvement of lipY in WE hydrolysis. Thus, Mtb can produce and use both major energy storage forms. TG and WE, and both forms are likely to be used for successfully going through dormancy. WE may also be a component of the cell wall lipids that control permeability.

SUMMARY OF THE INVENTION

With the foregoing in mind, the present invention advantageously provides a method of inducing latency in *Mycobacterium*, the method comprising growing a pure culture of *Mycobacterium* exposed to multiple stress conditions, the stress conditions including at least a low nutrient culture medium without glycerol, a low pH, a relatively high level of carbon dioxide and a relatively low gas phase oxygen level.

A latent culture of *Mycobacterium* growing in vitro is particularly useful in evaluating the effectiveness of antimicrobial compounds against this form of the organism, which is prevalent throughout the world in infected but asymptomatic persons. Before the present invention, it was difficult to test drug effectiveness against latent Mtb due to the lack of an easily reproducible model system. Accordingly, the present invention discloses an in vitro model of latent mycobacterial infection which is useful in testing antimicrobials for activity against the infection in its latent stage.

The method of the invention includes growing the Mtb in a low nutrient medium comprising approximately 10% Dubos medium, preferably at a pH of approximately 5 and in an atmosphere relatively high in level of carbon dioxide, at approximately 10%. Additionally, the atmosphere includes a relatively low oxygen level of approximately 5%. Preferably, in the method, the *Mycobacterium* is a strain of *Mycobacterium tuberculosis*.

Another embodiment of the present invention includes a method of inducing a pure culture of *Mycobacterium* to become rifampicin resistant and to store an increased lipid content, two hallmarks of latency, the method comprising growing the culture simultaneously exposed to multiple stress conditions, the stress conditions including at least a low nutrient culture medium without glycerol, a low pH, a relatively high level of carbon dioxide and a relatively low gas phase oxygen level.

The present invention also includes a pure culture, and even a single isolated cell of resistant *Mycobacterium* generated according to the method disclosed.

The invention includes an in vitro model of latent tuberculosis, the model comprising an isolated culture of THP1 derived macrophages containing ingested *Mycobacterium tuberculosis* bacteria and incubated under hypoxic conditions for a time sufficient for the bacteria to accumulate increased lipids therein. More broadly, the invention also provides an in vitro model of latent mycobacterial infection, the model comprising an isolated culture of THP1 derived macrophages containing ingested *Mycobacterium* spp. cells and incubated under hypoxic conditions for a time sufficient for the bacteria to accumulate increased lipids therein. More broadly still, the invention teaches an in vitro model of mycobacterial infection, the model comprising an isolated culture of THP1 derived macrophages containing ingested *Mycobacterium* spp. cells.

With regard to the various models disclosed in the invention, the teachings also comprise a method of making a model of latent tuberculosis, the method including inducing cultured THP1 cells to differentiate into macrophages; infecting the macrophages with *Mycobacterium tuberculosis* bacteria; and incubating the infected macrophages under hypoxia, particularly wherein incubating is for a time sufficient for the bacteria to accumulate increased lipids therein, a hallmark of latency. This method is, in general, also be applicable to other *Mycobacterium* species as well.

The various in vitro models of latent tuberculosis and mycobacterial infection herein disclosed are useful in evaluating compounds for effectiveness against these bacterial pathogens.

BRIEF DESCRIPTION OF THE DRAWINGS

Some of the features, advantages, and benefits of the present invention having been stated, others will become apparent as the description proceeds when taken in conjunction with the accompanying drawings, presented for solely for exemplary purposes and not with intent to limit the invention thereto, and in which.

DETAILED DESCRIPTION OF THE PREFERRED EMBODIMENT

Figure 1:
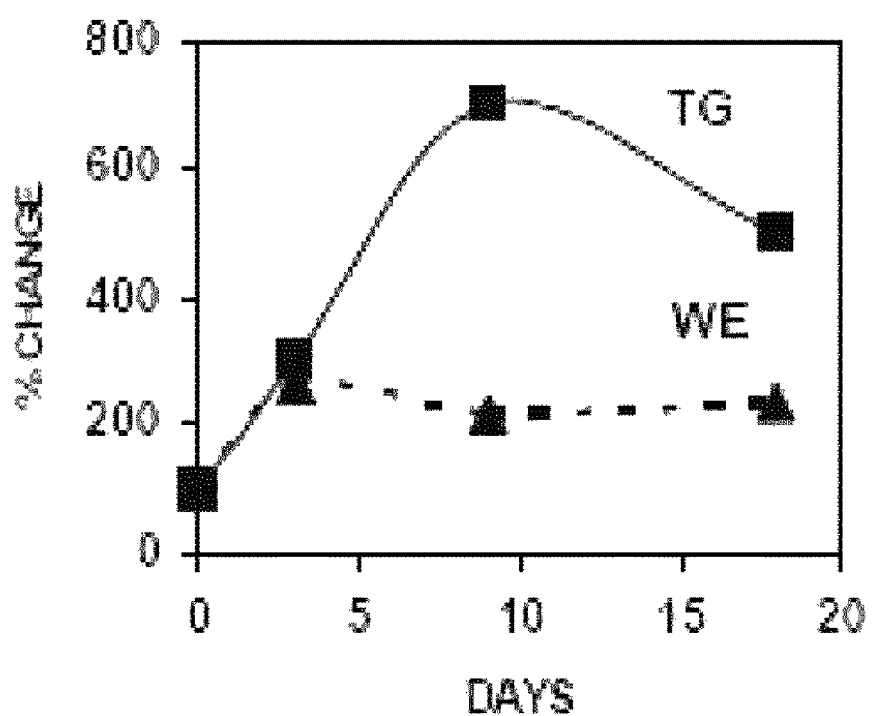
FIG. 1 is a demonstration of the accumulation of storage lipids in Mtb cells treated for the indicated periods under the multiple stress conditions, according to an embodiment of the present invention; TLC was performed as described; the plates were charred and quantitation was done by densitometry.

The present invention will now be described more fully hereinafter with reference to the accompanying drawings, in which preferred embodiments of the invention are shown. Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. Any publications, patent applications, patents, or other references mentioned herein are incorporated by reference in their entirety. In case of conflict, the present specification, including any definitions, will control. In addition, the materials, methods and examples given are illustrative in nature only and not intended to be limiting. Accordingly, this invention may be embodied in many different forms and should not be construed as limited to the illustrated embodiments set forth herein. Rather, these illustrated embodiments are provided so that this disclosure will be thorough and complete, and will fully convey the scope of the invention to those skilled in the art. Other features and advantages of the invention will be apparent from the following detailed description, and from the claims.

With the foregoing in mind, an in vitro dormancy model that can be adapted to drug screening would help to discover antilatency drug candidates, in vitro models suitable for such screening are urgently needed. A number of different stresses have been applied to Mtb in vitro in an attempt to generate a dormant state and gene expression changes have been investigated. Most of these models involve single stress factors such as oxygen depletion, nutrient deprivation, NO treatment and acidic conditions. The gene expression changes during combined nutrient deprivation and 10% and 0.2% oxygen stress on stationary phase cultures were investigated. Some of these stress conditions such as prolonged nutrient starvation caused Mtb to become highly Rif-resistant but accumulation of storage lipids was not tested. On the other hand hypoxic conditions we used that caused TG accumulation did not develop resistance to 5 μg/ml Rif (unpublished). The non-replicating persistence-1 (NRP-1) condition was reported to cause resistance to a lower concentration of Rif (1 μg/ml) but lipid accumulation was not tested. We suggest that both Rif-resistance and lipid storage are hallmarks of dormancy. Since individual stress conditions do not allow the pathogen to fully meet these criteria, we attempted to mimic the in vivo conditions by applying multiple stresses thought to be encountered in vivo by Mtb and tested whether the pathogen would accumulate storage lipids and develop Rif-resistance. Bacilli within granulomas encounter low oxygen (5%) but not hypoxia, high $CO_2$ (10%) concentrations, low nutrient levels and acidic pH. Based on these reports, we used 5% $O_2$, 10% $CO_2$, pH 5.0 and 10% Dubos medium in a multiple stress in vitro model. Our preliminary results show that the combination of the four stress factors leads to accumulation of storage lipids (TG and WE), development of Rif-resistance and gene expression changes thought to be associated with dormancy. Some of the gene expression changes are similar to those found in the pathogen from infected lungs of hosts, including primates and a human TB patient.

Both Rif-resistance and storage lipid accumulation are associated with dormancy. However, the commonly used in vitro hypoxia model, does not show both of these characteristics. Therefore we developed a novel multiple stress model that applies four different stresses that the pathogen is thought to encounter in the host. We grew Mtb cultures in low pH (pH 5.0), low nutrient (10%) Dubos medium without glycerol, with high (10%) $CO_2$ and low (5%) oxygen gas phase.

Mtb cultures in 10% Dubos (Difco) medium at pH 5.0 at an OD 600 of 0.2 were maintained under 5% $O_2$+10% $CO_2$+ 85% $N_2$ by replacing the air phase every other day; oxygen levels did not change significantly during the two day period. After monitoring the progressive changes that happened to the pathogen, we chose to harvest cells at 3, 9 and 18 days under such conditions for more detailed studies. These studies included examination of storage lipids, antibiotic (Rif and INH)-resistance, gene expression changes directly relevant to storage lipid synthesis by quantitative real time PCR (qPCR), and gene expression profiles by microarray analyses. TLC showed that WE and TG accumulated under the multiple stress conditions reaching near maximal levels by 9 days FIG. 1.

The major wax ester was oleyl oleate and the major fatty acids in the TG were C16 and C18 with less C26 (data not shown). Under these conditions more WE accumulated than TG in absolute amounts. Control samples at pH 7.0 or pH 5.0 without additional stress showed no increase in storage lipids.

Figure 2:
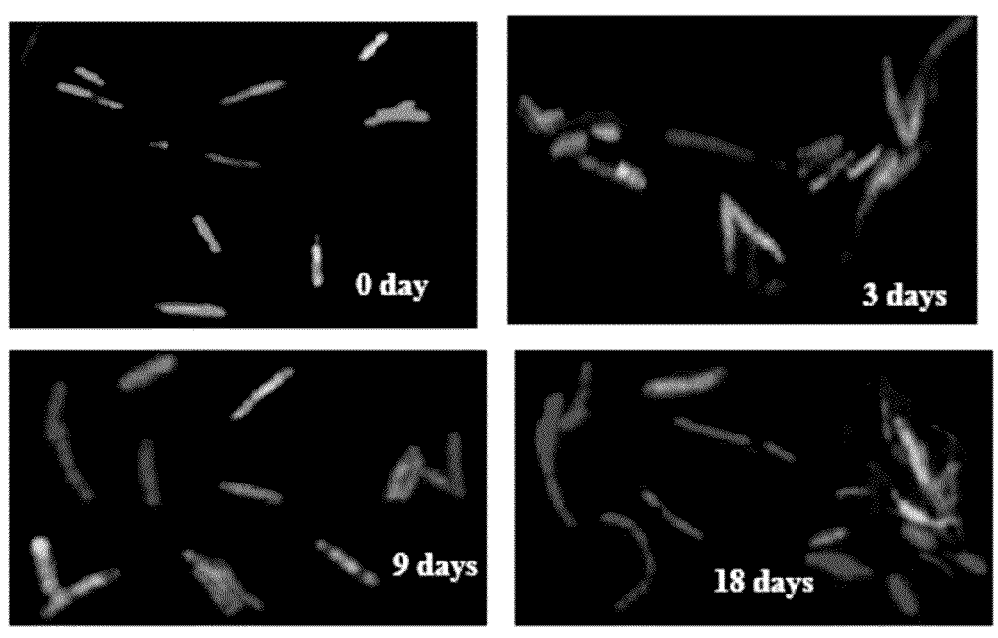
FIG. 2 shows increasing lipid storage bodies in Mtb cells with increasing periods of multiple stress; non-acid fast staining cells (green) and lipid storage body staining (red) increased with time under multiple stresses; cells were stained with Auramine-O and Nile Red and examined by confocal laser scanning microscopy (Leica TCS SP5) with Z-stacking to get the depth of the scan field; scanned samples were analyzed by LAS AF software for image projection.
Figure 3:
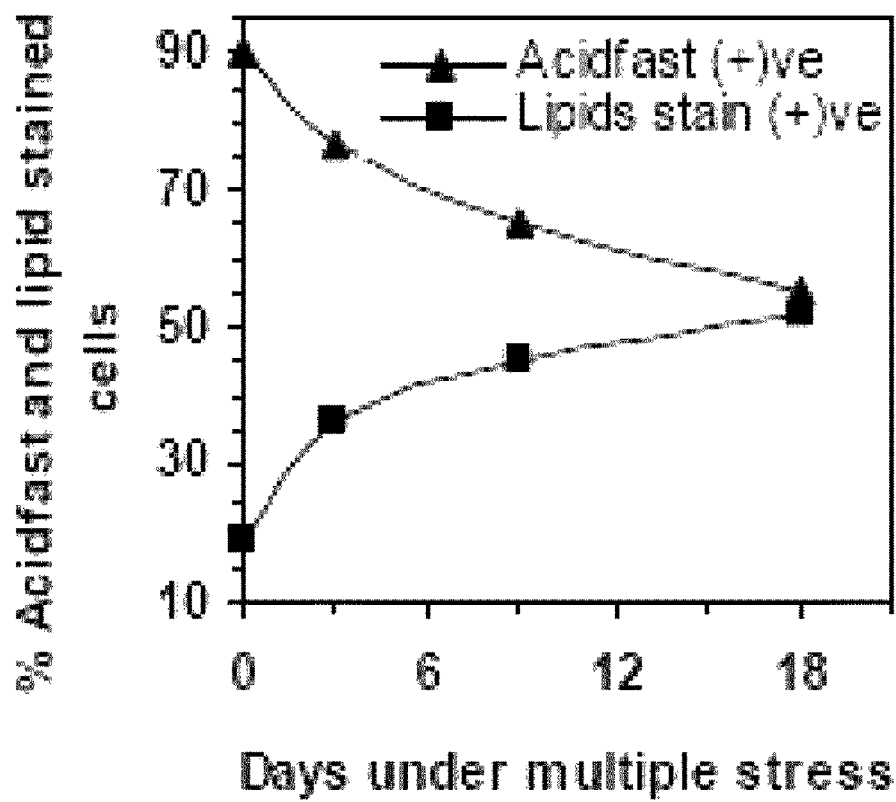
FIG. 3 shows an increase in the percentage of lipid-stained cells and decrease in percentage of acidfast stained cells in Mtb culture when subjected to multiple stresses in vitro.

Nile red staining revealed storage lipid accumulation under the multiple stress conditions. It is well known that Mtb cultures contain a heterogeneous population of cells under different physiological states. As the culture was subjected to multiple stress factors we observed decrease in acid fast staining cells with increasing lipid body staining cells from a barely detectable level to a significant percentage of the total cells by 18 days (FIGS. 2, 3).

Figure 4:
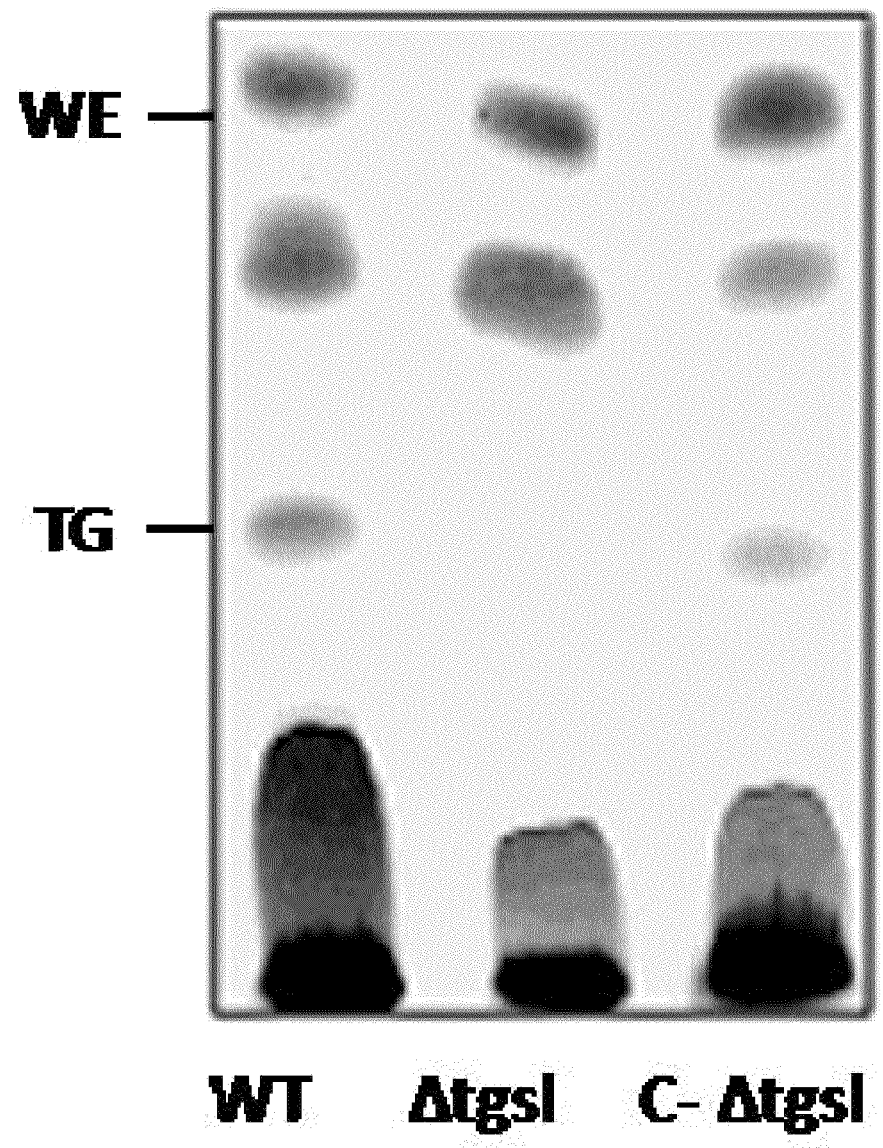
FIG. 4 depicts TG accumulation by tgs1 (Rv3130c) and restoration of TG accumulation by complementation under 18 days of multiple stress; equal amounts of lipid were subjected to TLC as in FIG. 1; C-Δtgs1, is a complemented mutant.

Drug resistance was tested by treatment with 5 µg/ml Rif for 5 days followed by serial dilution and plating. By 9 days about 10% of the cells were found to be Rif resistant whereas the starting culture contained about 0.03% Rif-resistant cells. Rif-resistance increased up to 18 days, sometimes reaching up to 25% at 5 µg/ml Rif. The tgs1 (Rv3130c) disruption resulted in the loss of Rif-resistance which was restored in the complemented mutant (Table 1). Hypoxic conditions, that were previously found to cause accumulation of storage lipids, did not cause the cells to develop detectable Rif-resistance at 5 µg/ml. The tgs1 (Rv3130c) disruption resulted in loss of TG accumulation under multiple stress. However the complemented mutant showed a level of TG accumulation comparable to the wild type (FIG. 4).

TABLE 1

Development of Rif-resistance in wild type H37Rv but not in Rv3130c mutant upon application of multiple stress: complementation restores Rif-resistance. Aliquots were either untreated or treated with Rif (5 µg/ml) or INH (0.8 µg/ml).

| Mtb | | Resistance to Antibiotics (%) | |
|---|---|---|---|
| strains | Days | INH (0.8 µg/ml) | Rif (5.0 µg/ml) |
| WT-H37Rv | 0 day | 0.034 (±0.02) | 0.037 (±0.027) |
|  | 9 day | 34.7 (±12) | 4.7 (±1.9) |
|  | 18 day | 84.4 (±17.5) | 12.5 (±3.4) |
| Δ-Rv3130c (Δ-tgs1) | 0 day | 0.011 (±0.01) | 0.025 (±0.019) |
|  | 9 day | 21.1 (±7.8) | 1.16 (±0.87) |
|  | 18 day | 31.2 (±13.1) | 1.89 (±0.9) |
| Comple-Δ-Rv3130c | 0 day | 0.041 (±0.02) | 0.029 (±0.01) |
|  | 9 day | 37.9 (±13.5) | 5.2 (±2.1) |
|  | 18 day | 91 (±19) | 11 (±4.5) |

ND, Not determined;
d, day.

Figure 5:
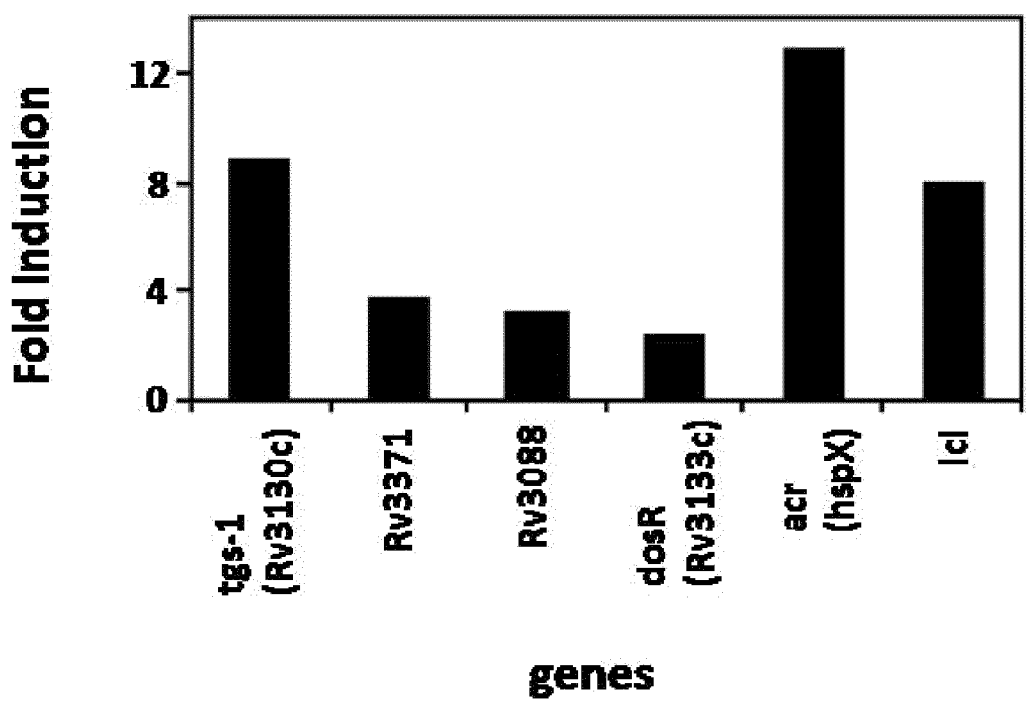
FIG. 5 shows real-time PCR measurements of transcript levels of tgs and stress responsive genes in Mtb H37Rv under in vitro multiple stress for 9 days; comparative $C_T$ method ($\Delta\Delta C_T$) was used to quantify and values obtained with starting aerated cells were used to calculate the fold induction.

Gene expression changes directly relevant to storage lipid accumulation were examined by real-time PCR. Among all the tgs genes, induction of tgs1 (Rv3130c) was by far the highest at 9 days under the multiple stress condition, followed by Rv3371 and Rv3088 (FIG. 5). Microarray analysis also indicated upregulation of Rv3371 under multiple stress condition (data not shown). Upregulation of Rv3088 probably resulted from the low pH as it has been previously reported to be induced under acidic stress. Up-regulation of Rv3371 is noteworthy as it was also shown to be up-regulated in human lung granuloma by microarray analysis. The degree of induction of tgs1 (Rv3130c) was comparable to that of icl and acr (hspX), genes previously reported to be induced during persistence. Our preliminary experimental results raise the possibility that lipid accumulation under different stress conditions might use different sets of tgs genes.

Figure 6:
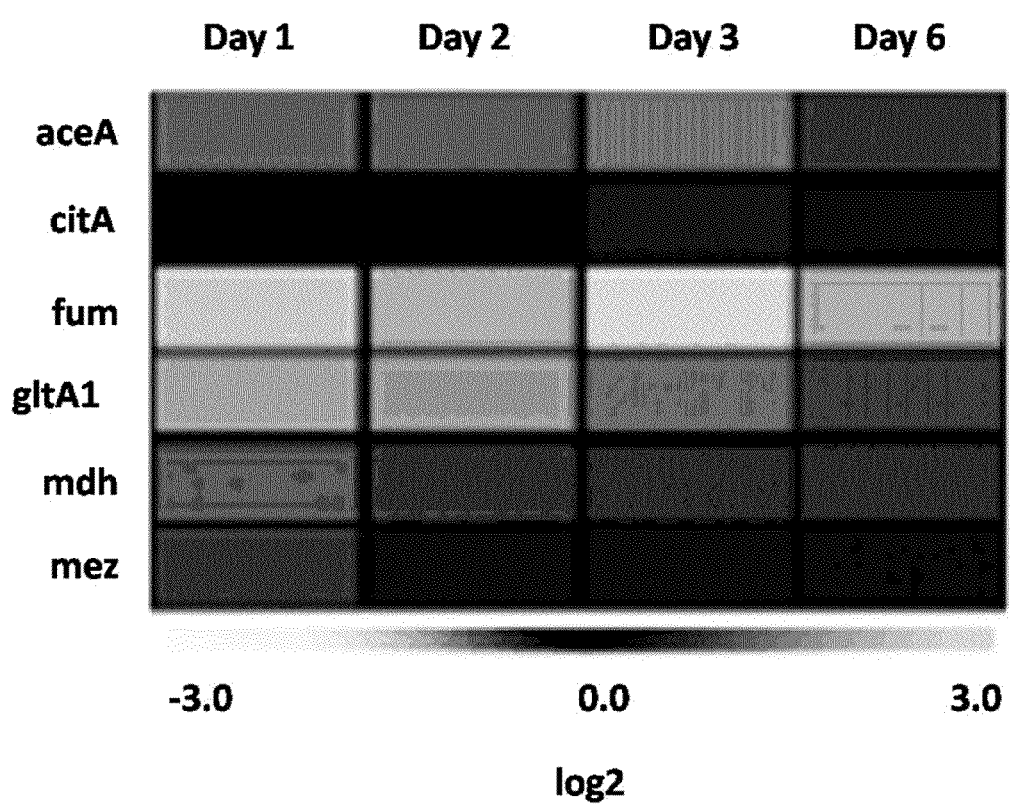
FIG. 6 shows expression profiles of genes encoding proteins involved in the glyoxylate cycle during the multiple stress treatment.

The TIGR Pathogen Functional Genomics Resource Center provided the Mtb genome microarray for this study. Under our multiple stress condition, genes that encode enzymes involved in glyoxylate cycle such as isocitrate lyase (aceA) and citrate synthase (gltA1) showed significant increase in expression for all time points examined (FIG. 6). From these data we infer that the metabolic regulation of cells adapting to the multiple stresses was similar to that observed in persistent bacilli adapting to the phagosomal environment of a macrophage. Under multiple stresses, Mtb showed shutdown of both ATP/NAD energy regeneration systems. While gene expression for anaerobic respiration was continuously increased at the later time points, the aerobic respiration was significantly repressed at all the time points. All the subunits encoding NADH dehydrogenase and the ubiquinol-cytochrome C complex were repressed more than 2-fold. In addition, the expression of the genes encoding ATP synthase subunits was repressed. Slowdown of the transcription/translation apparatus was evident during the multiple stresses. Many genes related to transcription and translation apparatus were all consistently repressed. Genes involved in modification of chromosome and cell division were repressed by the multiple stresses. The expression level of the gene cluster, mas, fad28, mmpL7, and ppsA-E, associated with phthiocerol dimycocerosate (PDIM) synthesis and transport, that was repressed at the beginning of the multiple stress treatment, gradually increased more than two-fold and remained high throughout the period of in vitro multiple stress. Further, the mas-like gene pks2, which is responsible for encoding a hepta/octa-methyl branched fatty acid synthase, was highly expressed. These changes are consistent with the report that dormant cells have thickened walls. We also found significant induction of the genes classified as the stress response genes (eg. hspX) that has been suggested to play a role in maintaining long term survival within the host. The gene array analysis results were verified by qPCR analysis of selected test genes. Repressed and induced gene transcript level changes indicated by microarray analysis were found to be consistent with the changes indicated by the qPCR method (data not shown).

Figure 7:
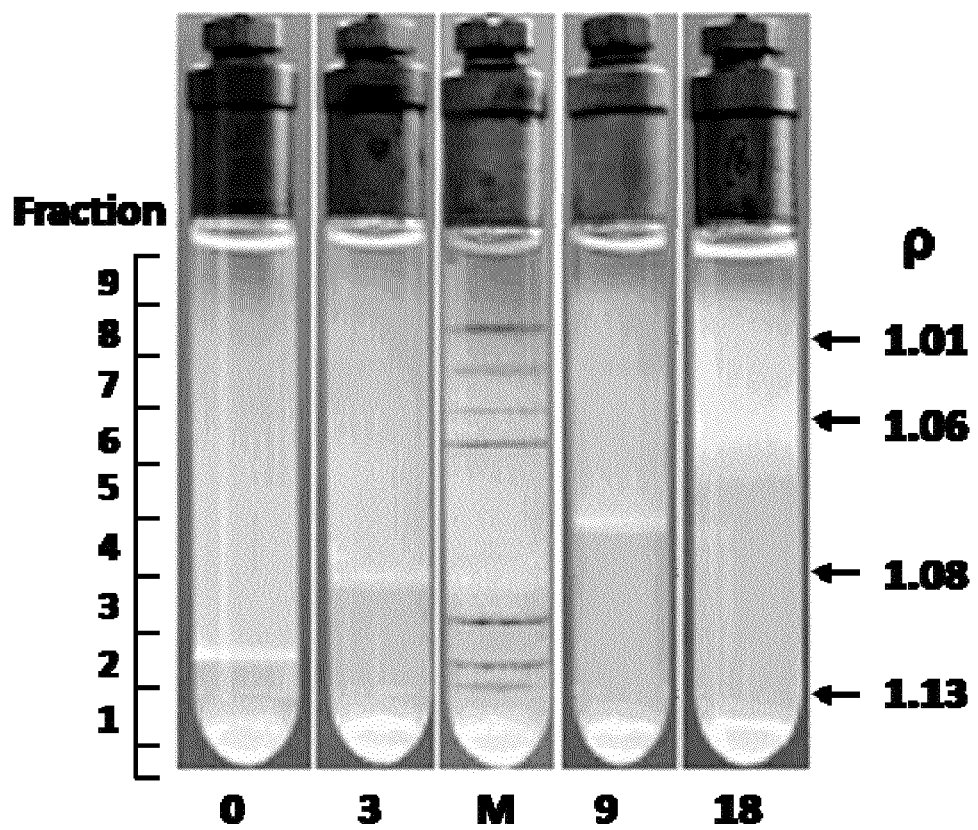
FIG. 7 depicts a decrease in buoyant density of Mtb cells subjected to multiple stresses; Mtb cells subjected to the multiple stresses were placed on the preformed gradient and centrifuged at 400 g for 20 min; the center tube is a 3 day cell sample mixed with density marker beads; Percoll® gradients were self-formed by centrifugation from a starting solution with a density of 1.0925 gm/ml; the densities of selected bead layers ($\rho$, in gm/ml) are given on the right and the positions of one ml fractions collected for analyses are at the left; numbers below the tubes indicate the number of days under multiple stress.

We investigated whether the lipid accumulation that occurs as a result of multiple stresses might be reflected in changes in buoyant density. We fractionated the culture on a Percoll® gradient in 10 ml Seton Easy-Seal polyallomer centrifuge tubes with Seton Noryl crown assembly. This procedure resolved cells based on buoyant density (FIG. 7). The banding pattern changed as the cultures were subjected to multiple stresses for increasing duration. These changes are consistent with the conclusion that application of multiple stresses caused progressive changes in lipid accumulation resulting in increasing percentages of cells in the lighter fractions. Auramine-O/Nile Red staining of the different fractions showed that with increasing periods under the multiple stresses, increasing percentage of cells became lipid-loaded and lost acid-fast staining (presumably dormant cells). Staining of Percoll® fractions from 18 day stressed cultures showed that the lighter fractions were more enriched in, lipid loaded cells that lost acid-fastness. After this long stress period most cells were in the lighter fractions (FIG. 7). Upon Percoll® density gradient fractionation of the 18-day multiple-stressed culture, the great majority of the cells were distributed in the lighter fractions. When Rif-resistance was assessed by the Alamar Blue dye method the lighter fractions showed a higher percentage of Rif-resistant cells (data not shown). The small number of heavier cells present in this culture showed Rif-susceptibility comparable to that of the starting culture.

Recent meta-analysis of Mtb microarray data from many in vitro and in vivo conditions that are thought to induce dormancy (Murphy and Brown, BMC Infect. Dis. I, 84-100, 2007) indicated that a set of genes possibly involved in lipid storage and utilization are highly upregulated. We have determined the transcriptional profile of the genes, selected on the basis of the meta-analysis by real-time PCR using 7500 Fast system (Applied Biosystem). Detection of transcriptional upregulation of the known dormancy-responsive genes such as hspx, icl and dosR (FIG. 1) is consistent with our conclusion that the multiple stress conditions induce dormancy. Seven of the 10 genes in the first priority group, such as Rv3130c along with a few other tgs genes (Rv3371, Rv1760), a few genes encoding potential hydrolases (lipX lipY, cut3), and fatty acyl-CoA reductase gene (Rv3391) showed upregulation. Three of the 21 genes in the next priority group showed upregulation under the multiple stress condition. One of them showed surprisingly high induction. The other two upregulated genes in this group were cut2 and lipZ. Only one gene (Rv2285, a tgs) in the third priority group showed upregulation. Among the tgs products that showed the highest enzymatic activity (when expressed in *E. coli*) only this tgs showed a preference for oleoyl-CoA. We already have mutant for this gene and this mutant showed the second most impaired ability to accumulate TG under hypoxia as indicated in the preliminary results presented in the application.

It is noteworthy that 7 of the 10 genes in the first priority group and 3 out of 21 genes from the second priority group and only one out of 17 in the third priority group showed upregulation. Since the prioritization is based on meta-analysis of the degree of their upregulation under a variety of conditions thought to induce dormancy, our results suggest that the multiple stress model reflects real dormancy and adds validity to our approach.

The tuberculous granuloma, which is thought to be a hypoxic environment, consists of a core of Mtb-infected macrophages surrounded by lipid-loaded macrophages, mononuclear phagocytes and lymphocytes enclosed by a fibrous cuff. The differentiation of macrophages into lipid-loaded macrophages in tuberculous granulomas is a well-documented observation and the secretion of cytokines by the infected lipid-loaded macrophages probably helps to maintain the granuloma. Histological studies revealed the presence of lipid-loaded macrophages in the granulomas of immunocompetent and HIV-1 infected patients with TB. Lipid-loaded macrophages contain abundant cytosolic stores of TG and cholesterol esters. A recent study showed that exposure of human macrophages to hypoxia (1% O2) converted them into lipid-loaded cells and *M. bovis* BCG infection induced the conversion of macrophages into lipid-loaded cells but the nonpathogenic *Mycobacterium smegmatis* failed to induce lipid body formation. Thus lipid bodies within Mtb-infected macrophages may have important roles in pathogenesis and possibly in latency. Human THP-1 monocytic cell line-derived macrophages (TDM) are known to be converted into lipid-loaded macrophages. Therefore they can serve as a more convenient experimental model for studies on Mtb mutants, because their use can avoid the variability in responses encountered in the use of human peripheral blood monocyte-derived macrophages and provide a readily available uniformly reproducible cell model suitable for high throughput screening of drug candidates. Lipid bodies have been found in Mtb obtained from patients with active disease. However, the origin of these lipids remains unknown. The pathogen inside the lipid-loaded macrophages might utilize fatty acids derived from the lipid bodies in the host cells to store lipids within Mtb for later use. Such a possibility was raised by the recent finding that adipocytes might be a home for dormant Mtb in humans. In fact, Mtb inside adipocytes were found to accumulate lipid bodies while becoming dormant, as indicated by their resistance to killing by drugs. The lipid bodies found in the pathogen from patients probably originate from the lipid bodies in the macrophages. Our results indicate that Mtb within lipid-loaded macrophages can use the host's TG to accumulate TG within the pathogen and this Mtb becomes Rif resistant meeting our criteria for dormancy.

A New Lipid-loaded Macrophage Model of Dormancy

Herein we disclose a newly developed THP-1 derived macrophage (TDM) system for infection with Mtb. THP-1 cells, differentiated into macrophages by treatment with 100 nM PMA for 3 days, were incubated for 3 days in 1% $O_2$ and 5% $CO_2$. Oil Red-0 staining revealed lipid droplet accumulation in such macrophages (FIG. 2). When the TDM were infected with Mtb at a multiplicity of infection (MOI) of 1.0 for 4 hr and incubated in 1% $O_2$/5% $CO_2$ for 3 days, lipid bodies accumulated in the host cells (FIG. 3). Mtb cells within the macrophages showed Nile Red stained lipid bodies (FIG. 4). Most Mtb cells showed loss of acid fast staining and thus stained only red; a few showed some acid fast and lipid staining (yellow).

We modified our experimental protocol to allow for longer incubation of infected macrophages. We infected TDM with Mtb at an MOI of 0.1 (1 *bacillus* per 10 macrophages) and extended the incubation of the infected TDM to 7 days under hypoxia. After 7 days, infected TDM were lysed and the cell debris was removed by centrifugation at 300 g for 10 min. The Mtb cells were pelleted by centrifugation at 3000 g for 10 min and washed. Lipids from the host-lipid bodies were extracted from the supernatant and the lipids from the pelleted To analyze fatty acid composition, host or Mtb TG was purified by preparative TLC and the methyl esters generated by BF3/methanol transesterification, were analyzed by capillary GC. The amount of fatty acids from the TG isolated from Mtb, recovered for TDM, is more than enough for such GC analysis (FIG. 6) pathogens were extracted. TLC analysis of the lipids revealed that TG in the host cells was markedly increased by incubation under hypoxia for 7 days and the levels of TG were lower in infected TDM under hypoxia (FIG. 5A). Lipids extracted from Mtb recovered from infected TDM were also analyzed by TLC. We detected increased TG level in Mtb cells recovered from TDM incubated under hypoxic conditions (FIG. 5).

The fatty acid composition of the TG from the pathogen was not identical to that of the host TG. C16:0, C18:0 and C18:1 fatty acids were the dominant components in both the pathogen and the host. Longer chain saturated fatty acids (C24. C26 and C28) that were present in the pathogen TG were absent in the host TG. We conclude that the TG that accumulated in the pathogen probably consisted of fatty acids from the host and some fatty acids generated within the pathogen.

Gene expression changes occurring in the pathogen within TDM were examined using a two-step real time PCR method. Briefly, total RNA was isolated and purified from a mixture of Mtb-infected TDM using Trizol (Invitrogen) and Qiagen RNeasy column purification method. Total RNA was DNase treated twice, purified through Qiagen mini elute RNeasy column, purity of RNA was checked at every step. Controls without reverse transcription (RT) verified lack of DNA contamination. First-strand cDNA, synthesized with exo-resistant random hexamers and Superscript III reverse transcriptase (Invitrogen) was used for multiplex PCR using many Mtb gene specific primer sets. All primers and Taqman probes were designed using VisualOMP6 software from DNA software, Inc (Ann Arbor. MI). The Taqman probes have a fluorescein reporter dye (FAM) at 5'-end and a Black Hole Quencher (BHQ) at 3'-end. Each multiplex and real-time PCR primer was checked for specificity and efficiency. Differences in Mtb specific gene transcripts were quantified by real-time PCR on generated multiplex-PCR products with nested Taqman primers and probes. The overall reliability and sensitivity of the two-step RT-PCR method to quantify gene expression profiling has been discussed in detail elsewhere. We have thus far done only a subset of genes thought to be relevant to lipid storage and metabolism (FIG. 7); icl was by far the most induced gene, consistent with the idea that the pathogen in TDM grows on fatty acids. It is noteworthy that lipY, that was previously shown by us to be involved in TG mobilization, was highly induced and some of the other lip genes also showed induction. dosR and tgs genes were also induced probably indicating their involvement in the storage of fatty acids derived from host-lipids as TG resynthesized within the pathogen, consistent with our hypothesis. fatp, that might be involved in fatty acid transport into the pathogen was also induced. Putative fabp genes also showed some induction. These results indicate that our hypothesis concerning storage and mobilization of host lipids by the pathogen has real validity.

We analyzed the resistance of Mtb recovered from TDM after a 7 day incubation under 20% $O_2$ or 1% $O_2$ to Rif and INH by cfu determination. TDM were infected with Mtb at an MOI of 0.1. Mtb cells inside TDM were exposed to antibiotic for 2 days prior to lysis of TDM and recovery of the bacilli. The recovered Mtb cells were diluted and plated on agar plates without antibiotic and incubated for 4 weeks after which cfus were enumerated. Antibiotic resistance is expressed as percentage of control without antibiotic. As indicated in Table 2, Mtb recovered from TDM incubated under 20% $O_2$ showed resistance to both antibiotics. Others have found development of Rif resistance in host cells. We found that Rif resistance increased significantly in Mtb recovered from TDM incubated under 1% $O_2$ for 7 days compared to normoxic conditions. These results indicate support for our hypothesis that lipid-loading of macrophages favor the entry of Mtb into dormancy.

Lipid-loaded Macrophage Model

In making further progress developing the macrophage dormancy model, we tested different MOI in the lipid loaded macrophage system. We assessed the viability of Mtb-infected lipid-loaded macrophages under hypoxia under different MOI. At MOI 1.0 or higher the host cell viability was seriously compromised. At MOI 0.1, after 7 days under 1% $O_2$, 40% of the original TDM population remained intact as an adhered monolayer and were loaded with lipid droplets. About 94% of these lipid-loaded TDM cells in the adhered monolayer were viable. These results support the notion that these lipid-loaded TDMs provide a TG-enriched sanctuary for Mtb, favoring its entry into dormancy.

TABLE 2

Increase in resistance of Mtb inside lipid-loaded macrophages to Rif and INH. Mtb within TDM incubated for 7 days under 20% $O_2$ or 1% $O_2$ was exposed to antibiotic for 2 days. Mtb cells were then recovered by lysis of TDM and plated on agar plates for cfu determination.

| Mtb recovered from TDM incubated | Resistance to Antibiotic | | | |
| --- | --- | --- | --- | --- |
| | Rif | | INH | |
| 7 days in | 1 µg/ml | 5 µg/ml | 0.1 µg/ml | 0.8 µg/ml |
| 20% $O_2$ | 9% | 4% | 25% | 12% |
| 1% $O_2$ | 68 ± 14% | 25 ± 2% | 100% | 68 ± 18% |

We originally suspected that Mtb utilizes the macrophage lipid bodies to acquire fatty acids and store them as TG within the pathogen to enable it to go through dormancy. To test this hypothesis, we labeled TDM lipids by incubating the cells with [$^{14}$C]acetic acid or [$^{14}$C]oleic acid, under 1% $O_2$ for 2 days. These cells were washed three times with sterile phosphate-buffered saline (PBS) to remove unincorporated radiolabel. Thin-layer chromatographic (TLC) analysis of the labeled lipids extracted from TDM showed that major part (about 60%) of the radioactivity in the lipids derived from labeled acetate and oleate was in TG that accumulated in TDM under 1% $O_2$. These pre-labeled cells were infected with Mtb at an MOI of 0.1 for 4 h under 1% $O_2$. Following infection, extracellular Mtb were removed by thoroughly washing the TDM monolayer with sterile PBS. Infected TDM were incubated for 5 more days under 1% $O_2$. The host lipids and lipids from Mtb recovered from the host cells were obtained and the lipids were analyzed by TLC. The fatty acid composition of the Mtb and host TG was analyzed by resolving the intact TG and fatty acid methyl esters derived from TG on reversed-phase silica-TLC and argentation-TLC. Analysis of intact TG from [$^{14}$C]acetate in TDM was composed of saturated and unsaturated fatty acids. However, the TG of Mtb was predominantly composed of saturated fatty acids as indicated by greater mobility on $AgNO_3$-impregnated TLC (FIG.

Figure 8:
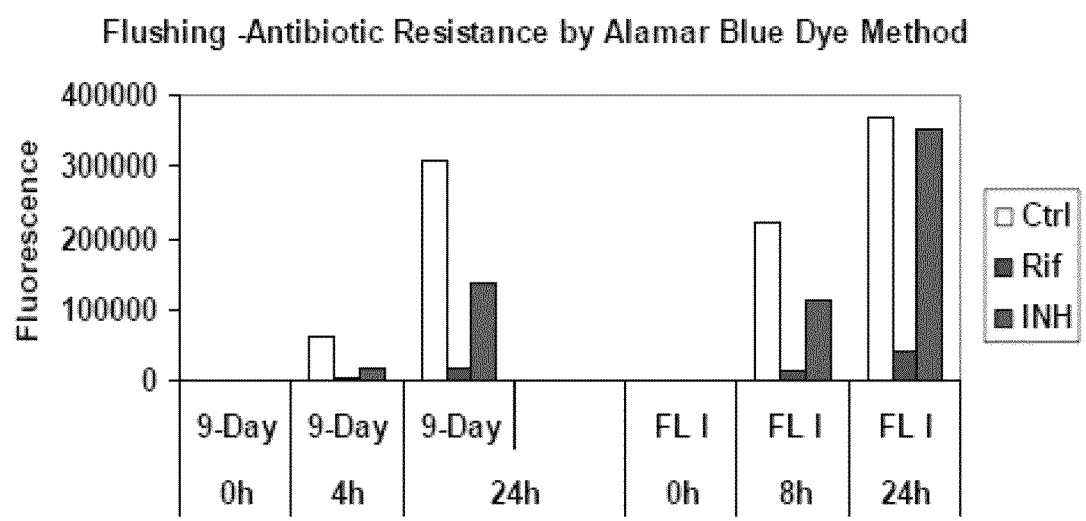
FIG. 8 is a bar graph showing that Alamar Blue assay reveals development of Rif resistance by multiple-stressed Mtb cultures; Mtb cultures subjected to multiple stresses were assayed by the specially adapted Alamar Blue method described in text for resistance to Rif and INH; fluorescence readings above 0 h controls are depicted.

8A). Analysis of fatty acid methyl esters prepared from TG isolated from TDM and Mtb indicated that the TG of Mtb, recovered from TDM labeled with [$^{14}$C]acetate, was composed primarily of saturated fatty acids, mostly $^{14}$C-16:0 and a very small quantity of $^{14}$C-18:0 fatty acids (FIG. 8). See also Table 3, below.

TABLE 3

Accumulation of radiolabeled TG by Mtb and mutants in lipid-loaded macrophages under hypoxia:

| | | DPM in TG | % of WT |
|---|---|---|---|
| $^{14}$C-Acetate | WT | 210,000 | 100% |
| | ΔRv3130c | 22,600 | 11% |
| $^{14}$C-Oleate | WT | 29,000 | 100% |
| | ΔRv3130c | 1470 | 5% |

Mtb recovered from [$^{14}$C]oleic acid-labeled TDM had TG that was distinctly different in fatty acid composition from the TG in TDM. While the $^{14}$C in TDM TG was predominantly in 18:0 (about 81% of total fatty acids), $^{14}$C in Mtb TG was mainly in unsaturated fatty acids (about 70% of total fatty acids). The identity of these fatty acids is to be determined. These results clearly indicate that Mtb acquires fatty acids from TDM lipid bodies for synthesizing TG as a potential energy source. The TG stored within the pathogen probably includes the fatty acids from the host lipids and fatty acids generated by modification and/or catabolism and resynthesis. The biochemical processes involved can be deduced only after further characterization of the TG that accumulates in the host and in the pathogen.

We also postulated that the Mtb tgs gene products may be pivotally involved in synthesizing TG within the Mtb cell from fatty acids acquired from host TG. To test this hypothesis, we infected the pre-labeled TDM with wild-type Mtb and tgs1 (Rv3130c) deletion mutant (ΔRv3130c) as described in the methods section. About 1% of the radiolabel in the TG in TDM was found in the TG isolated from Mtb. We quantitated the radioactivity in the TG of Mtb and ΔRv3130c recovered from TDM. The results indicate that TG accumulation by the Δ3130c was decreased by 90-95% when compared to the wild-type (Table 3). These results additionally suggest that Rv3130c plays an essential role in the accumulation of TG by Mtb within lipid-loaded macrophages.

Figure 9:
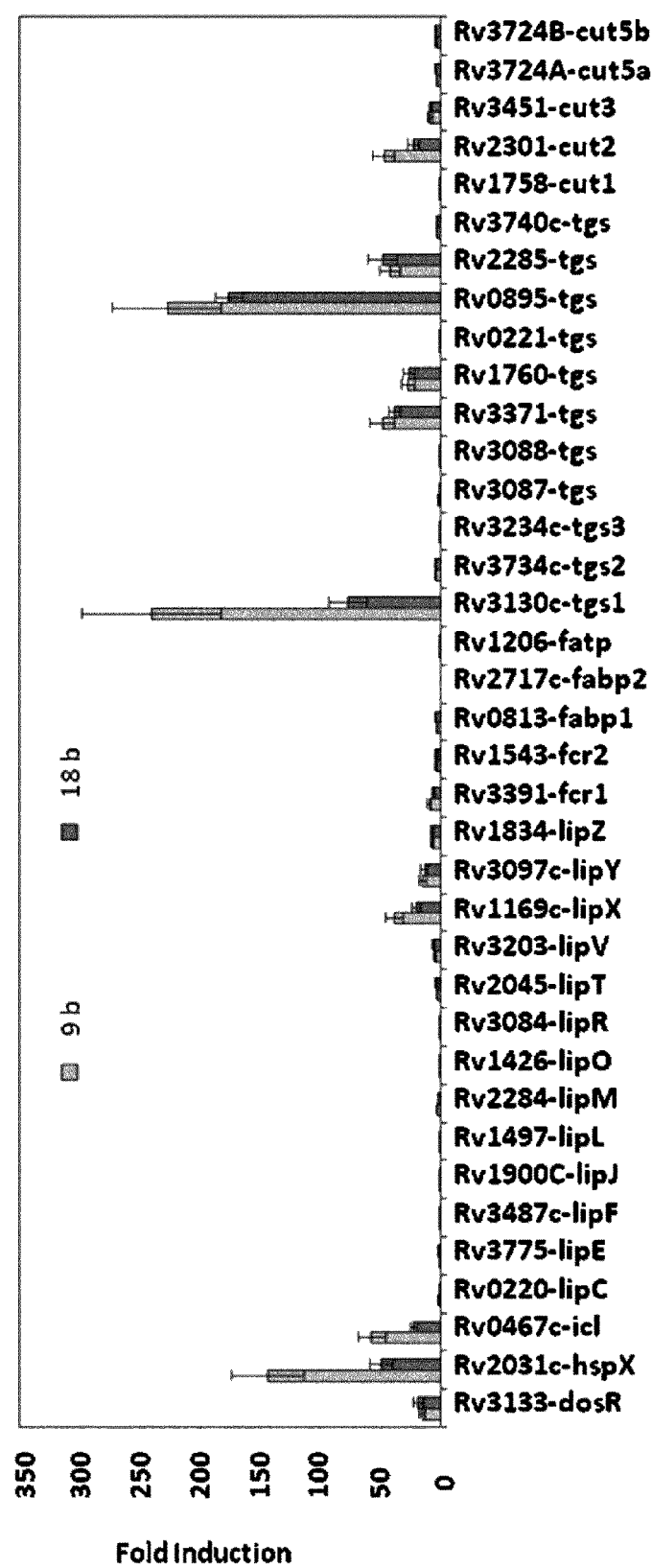
FIG. 9 shows real time PCR measurement of transcripts levels of a subset of selected dormancy metabolism and stress responsive genes in Mtb H37Rv under in vitro multiple stresses for 9 and 18 days; a relative quantitation method (ddCt) was used with the 7500 Fast real time system; samples of starter cultures were used as calibrator to calculate the fold induction.

In order to visualize the Mtb inside lipid-loaded host cells, infected TDM after 7 days under hypoxia were fixed with 4% paraformaldehyde and stained for Mtb with carbolfuschin followed by methylene blue or hematoxylin and eosin to stain the host cell. Mtb inside TDM were also stained with the mycolic acid-specific fluorescent dye Auramine-O followed by Nile Red which stains neutral lipids. Interestingly, as seen in FIG. 9, the Mtb-infected TDM which were incubated under hypoxia for 7 days appeared to be fusing together. It is probable that these TDM are in the process of forming multinucleate giant cells (asterisk in FIG. 9) which are known to be present in the hypoxic environment of the granuloma in close vicinity to lipid-loaded macrophages. These observations support the hypothesis that this lipid-loaded macrophage system is a good model for in vivo latency.

Figure 10:
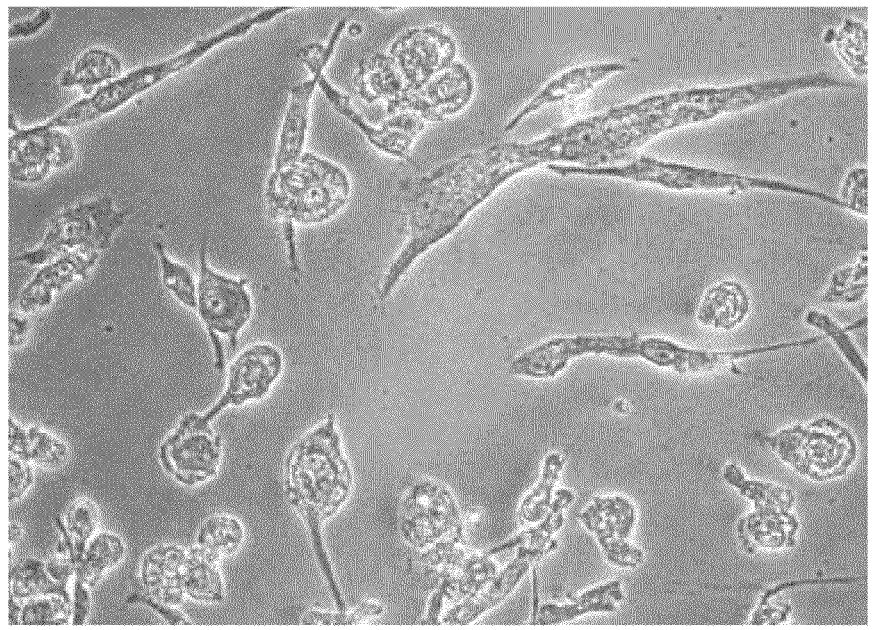
FIG. 10 are photomicrographs where Oil Red-0 staining reveals lipid droplet accumulation in TDM incubated for 3-days in 1% $O_2$, 5% $CO_2$ (a) compared to O-day control (b)
Figure 10:
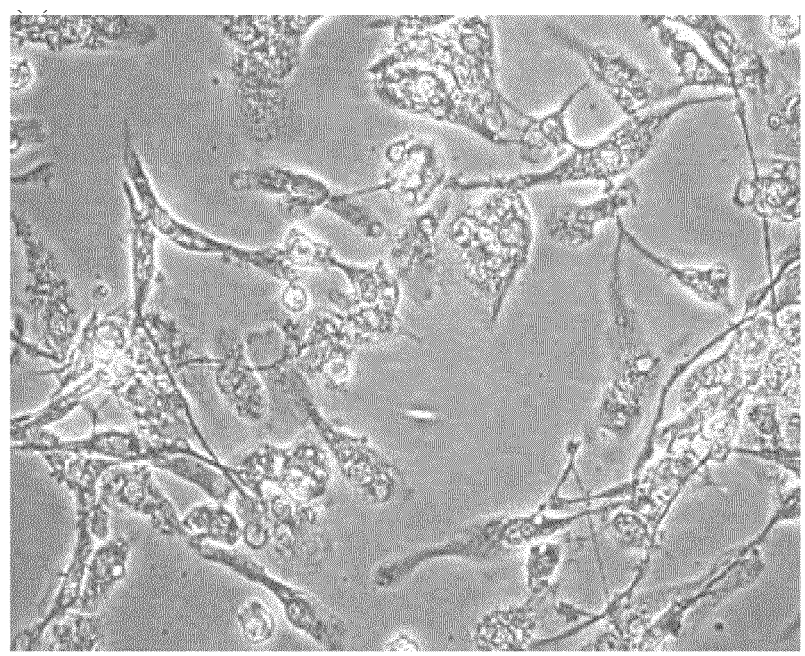
Figure 11:
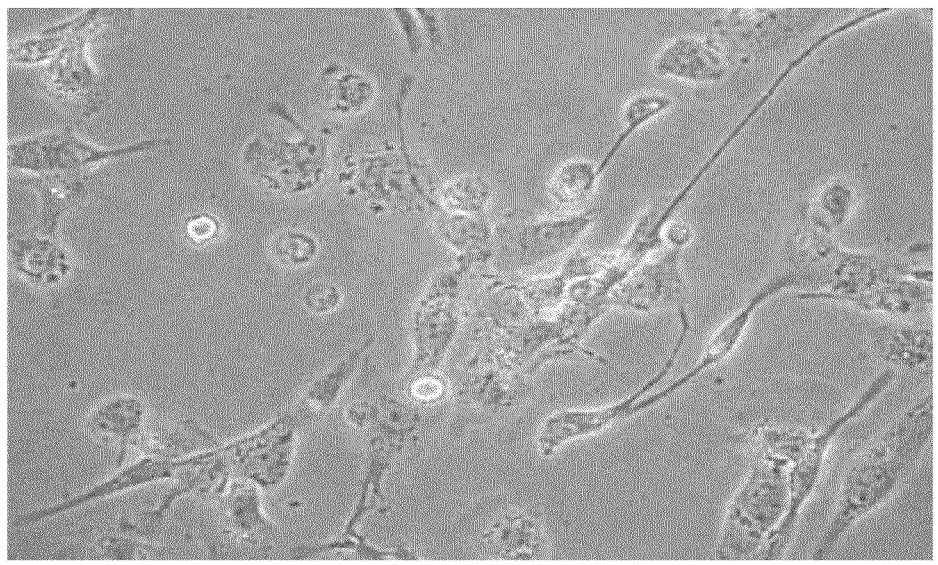
FIG. 11 indicates the increase in lipid bodies in TDM infected with Mtb and subjected to hypoxia for 0 and 3-days.
Figure 11:
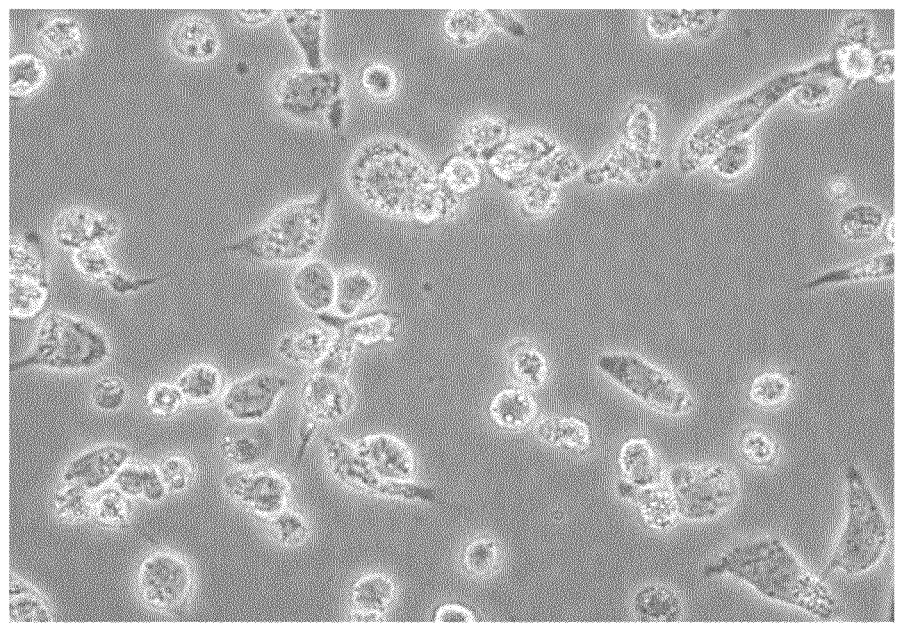
Figure 12:
FIG. 12 shows Mtb within TDM stained with Auramine-O and Nile Red showing spherical fluorescent lipid bodies and lack of acid fast staining.
Figure 13:
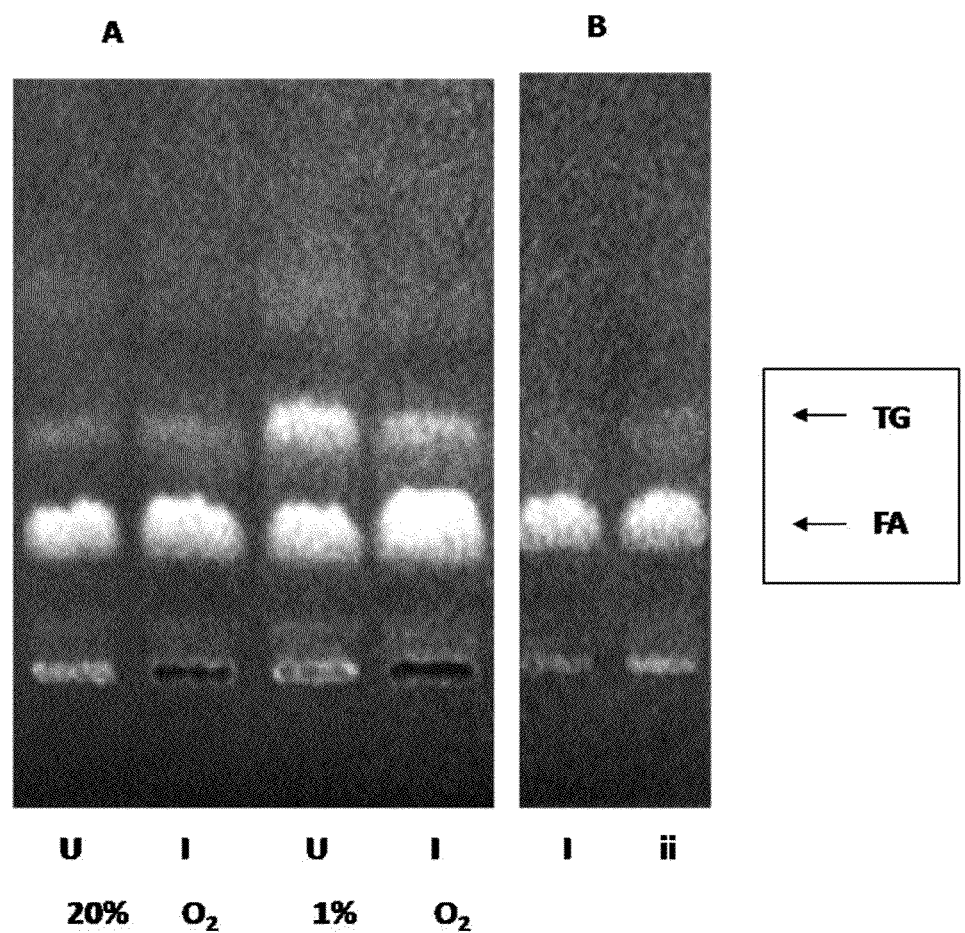
FIG. 13 shows that TG accumulated by TDM under hypoxia is utilized by Mtb; in A, lipids from uninfected (U) and infected (I) TDM, incubated in 20% $O_2$ or 1% $O_2$ for 7 days after infection, were resolved on TLC and visualized under UV light after spraying with 2',7'-dichlorofluorescein; in B, lipids of Mtb recovered from TDM incubated in 20% $O_2$ (i) or 1% $O_2$ (ii); solvent was hexane-ether-formic acid (90: 10:1, v/v/v) TG, triacylglycerol, FA, fatty acids.
Figure 14:
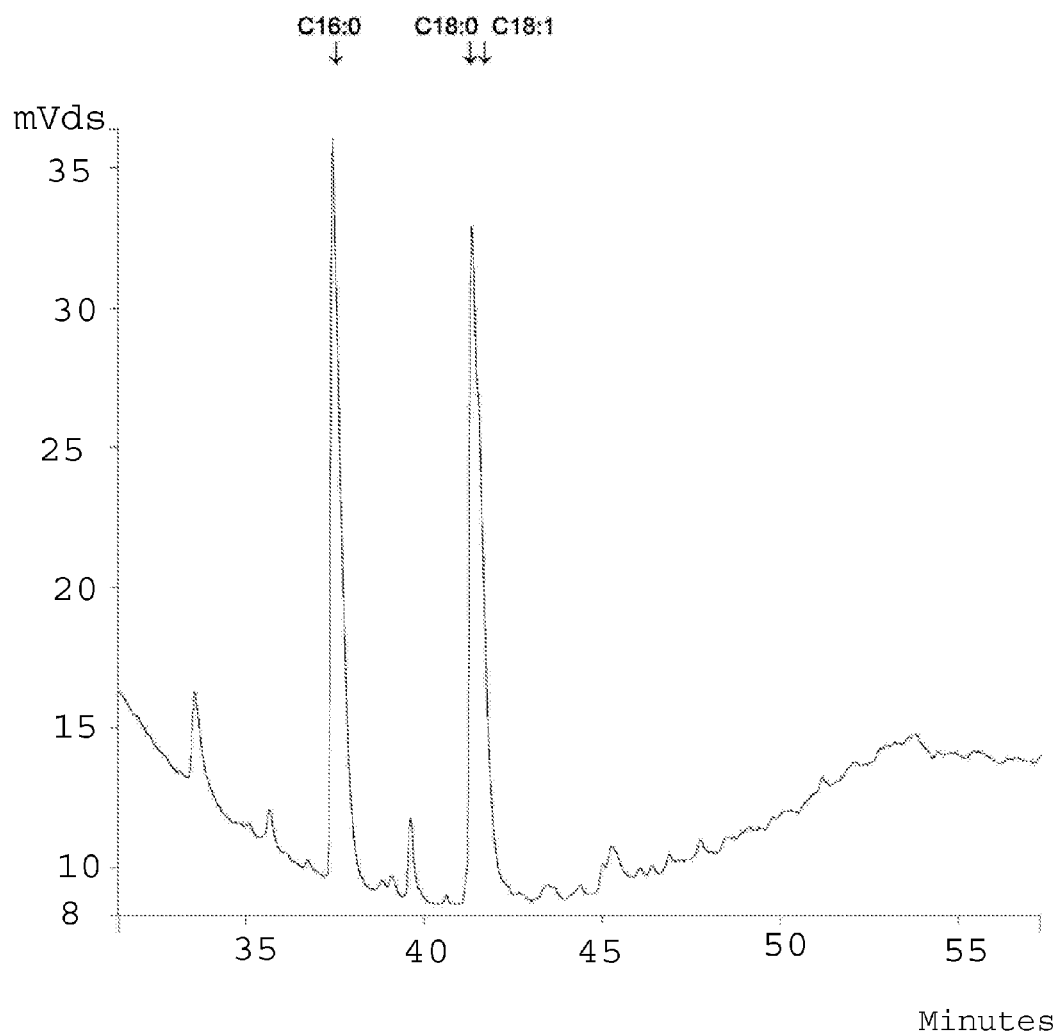
FIG. 14 depicts the fatty acid composition of TG from Mtb recovered after TDM infection; after infection with Mtb, TDM were incubated under 1% $O_2$ for 7 days; TG from Mtb isolated from TDM was purified by preparative TLC. Fatty acid methyl esters were prepared from Mtb TG and analyzed using a Varian CP-TAP CB column attached to a Varian CP-3900 gas chromatograph under a temperature control program.
Figure 15:
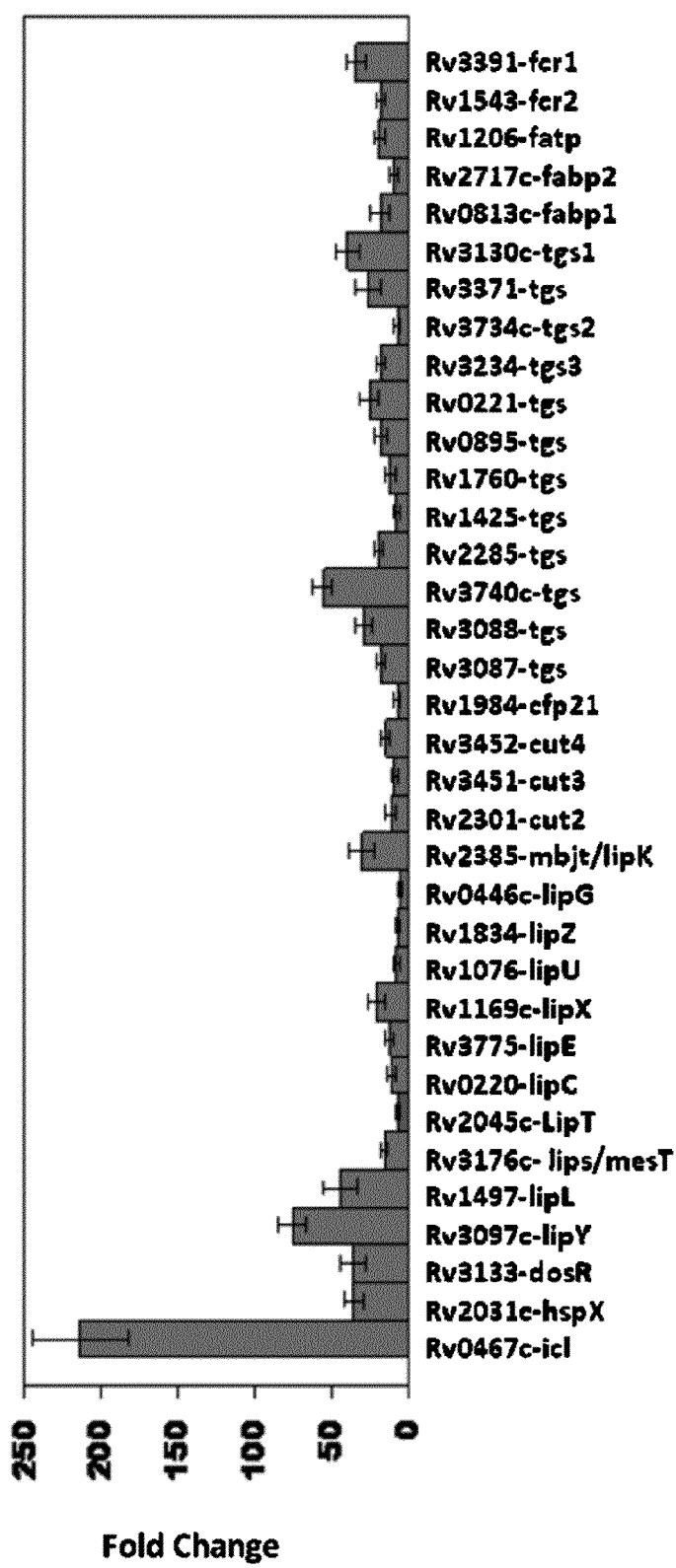
FIG. 15 depicts transcriptional profiling of genes in Mtb H37Rv from infected TDM under hypoxia.
Figure 16:
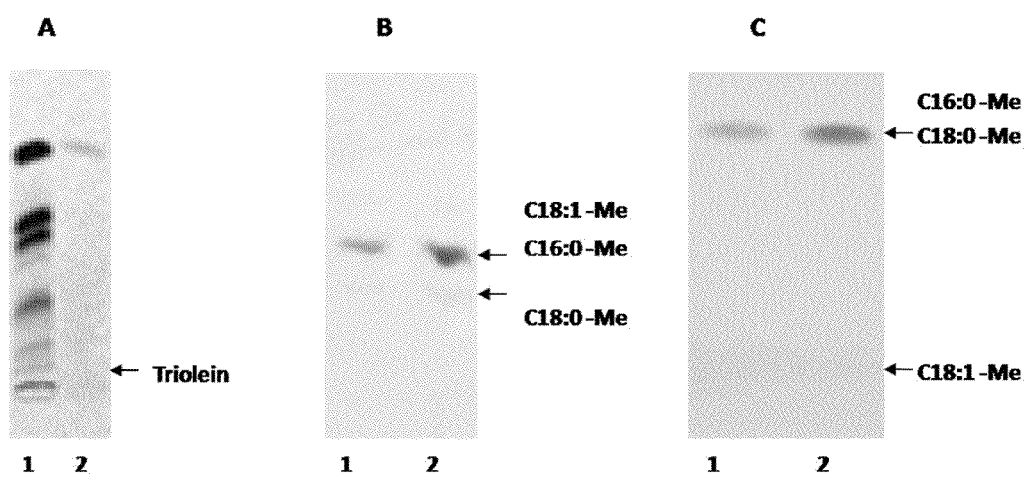
FIG. 16 shows that Mtb inside [$^{14}$C]acetate-labeled lipid-loaded macrophages mobilizes host lipids and accumulates TG enriched in saturated fatty acids; in A, $AgNO_3$-impregnated silica-TLC purified from [$^{14}$C]acetate-labeled lipids of infected macrophages (lane 1) and from Mtb recovered from such macrophages (lane 2); solvent system is 1% methanol in chloroform; in B, is shown reversed-phase TLC analysis of fatty acids methyl esters of TG from infected macrophages (lane 1) and from Mtb recovered from infected macrophages (lane 2); the solvent system is acetonitrile:methanol:water: acetic acid (30:70:5:1, by volume); in C. $AgNO_3$-impregnated silica-TLC of fatty acids methyl esters of TG from infected macrophages (lane 1) and from Mtb recovered from infected macrophages (lane 2); the solvent system is hexane: diethyl ether: acetic acid, 94:4:2, v/v/v, (developed twice)
Figure 17:
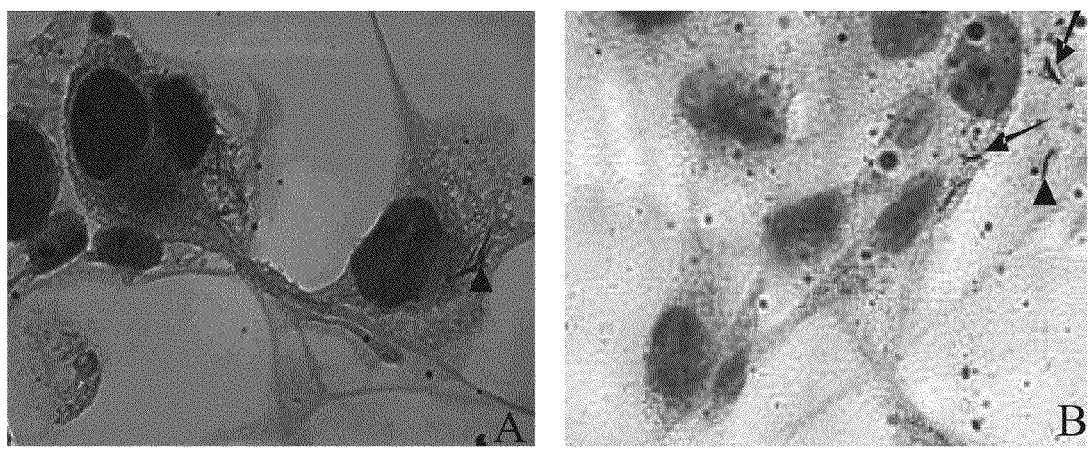
FIG. 17 shows TDM infected with Mtb and incubated under hypoxia appear to fuse together; TDM infected with Mtb at an MOI of 0.1 and incubated for 7 days under 1% $O_2$ were stained with carbolfuschin followed by hematoxylin and eosin (A) or carbolfuschin followed by methylene blue (B); arrows show Mtb.
Figure 18:
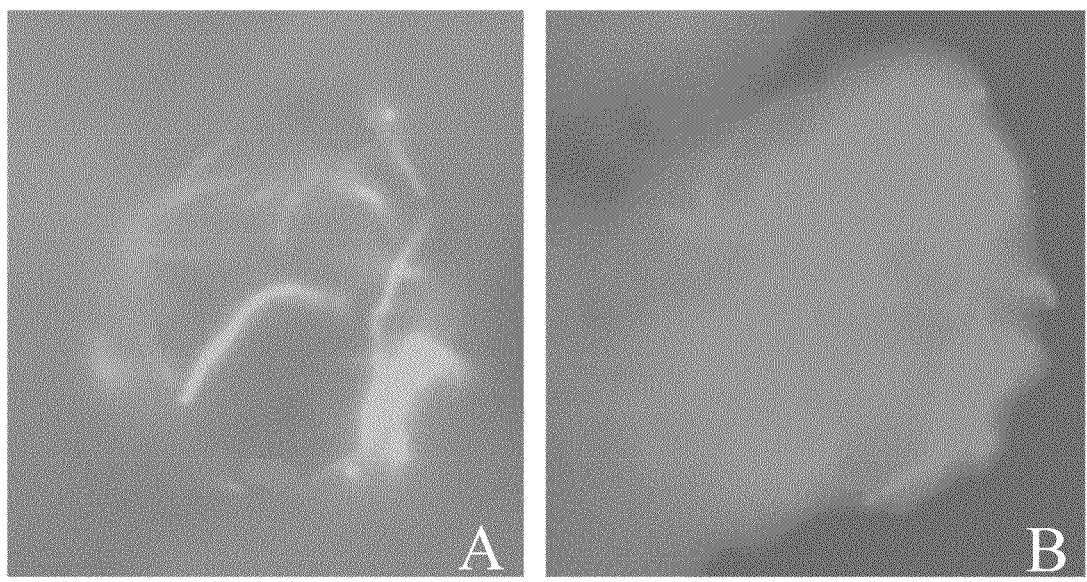
FIG. 18 shows Mtb inside TDM that accumulate neutral lipids lose acid-fastness; intact TDM harboring Mtb were fixed with 4% paraformaldehyde overnight and stained with the fluorescent mycolic acid staining dye Auramine-O (A) followed by the neutral lipid stain Nile Red.

Individual Mtb cells inside TDM that accumulated neutral lipids, as indicated by Nile Red staining, lost acid-fastness as shown by weak or total loss of Auramine-O staining (FIG. 10). Conversely, Mtb cells which stained strongly with Auramine-O did not accumulate neutral lipids. This accumulation of neutral lipids and loss of acid-fastness by a subset of Mtb cells within lipid-loaded TDM under hypoxia, correlates well with our data in the Preliminary Results, that demonstrated the development of Rif resistance by about 25% of the Mtb population and increase in TG within Mtb from TDM under the same conditions. Since then, we have reconfirmed these results with additional experiments.

Based on these results, the multiple stress in vitro latency model disclosed herein appears to be the best one available for screening chemicals to discover drug candidates that can eliminate latent pathogen. Accordingly, in the drawings and specification there have been disclosed typical preferred embodiments of the invention and although specific terms may have been employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

That which is claimed:

1. A method of inducing a pure culture of *Mycobacterium* to become rifampicin resistant and to store an increased lipid, the method comprising growing the culture simultaneously exposed to multiple stress conditions, the stress conditions including at least a low nutrient culture medium without glycerol, wherein said low nutrient medium is 10% Dubos medium or less, a low pH, wherein said low pH is a pH of 5 or less, a relatively high level of carbon dioxide, wherein said relatively high level of carbon dioxide is 10% or higher, and a relatively low gas phase oxygen level, wherein the relatively low oxygen level is 5% or lower.

2. The method of claim 1, wherein the *Mycobacterium* is a strain of *Mycobacterium tuberculosis*.

* * * * *